United States Patent
Woo et al.

(10) Patent No.: US 7,485,326 B2
(45) Date of Patent: Feb. 3, 2009

(54) ORAL MICROEMULSION COMPOSITION COMPRISING BIPHENYLDIMETHYLDICARBOXYLATE AND SILYBIN

(75) Inventors: Jong Soo Woo, Suwon-si (KR); Si Young Jung, Suwon-si (KR); Ae Guk Kim, Incheon (KR)

(73) Assignee: Hanmi Pharm Co., Ltd., Kyungki-do (KR)

( * ) Notice: Subject to any disclaimer, the term of this patent is extended or adjusted under 35 U.S.C. 154(b) by 292 days.

(21) Appl. No.: 10/576,196

(22) PCT Filed: Oct. 21, 2004

(86) PCT No.: PCT/KR2004/002698

§ 371 (c)(1),
(2), (4) Date: Apr. 17, 2006

(87) PCT Pub. No.: WO2005/037249

PCT Pub. Date: Apr. 28, 2005

(65) Prior Publication Data

US 2007/0141185 A1    Jun. 21, 2007

(30) Foreign Application Priority Data

Oct. 21, 2003    (KR) .................... 10-2003-0073462

(51) Int. Cl.
*A61K 36/28*    (2006.01)
*A61K 36/00*    (2006.01)
*A61K 31/765*    (2006.01)

(52) U.S. Cl. ............... 424/764; 424/725; 514/452; 514/557

(58) Field of Classification Search ............... None
See application file for complete search history.

(56) References Cited

U.S. PATENT DOCUMENTS 6,322,805 B1 * 11/2001 Kim et al. ............ 424/426
6,428,821 B2 * 8/2002 Woo et al. ............ 424/764
7,078,064 B2 * 7/2006 Zabrecky ............ 424/757

FOREIGN PATENT DOCUMENTS

KR    1999-39932 A    6/1999

OTHER PUBLICATIONS

Kim et al. J. Controlled Release. 2001. vol. 70, pp. 149-155.*

* cited by examiner

*Primary Examiner*—Christopher R. Tate
(74) *Attorney, Agent, or Firm*—Sughrue Mion, PLLC

(57) ABSTRACT

A microemulsion composition comprising biphenyldimethyldicarboxylate (BDD) and silybin or a derivative thereof, or a *Carduus marianus* extract containing silybin and derivatives thereof, as active ingredients; a co-surfactant; a surfactant; and an oil provides a synergistic therapeutic effect for liver diseases due to the complementary work of the two kinds of active ingredients having different working mechanisms without any adverse side effect or an antagonism, and high *in vivo* bioavailabilies of both of the active ingredients, when orally administered.

8 Claims, No Drawings

ORAL MICROEMULSION COMPOSITION COMPRISING BIPHENYLDIMETHYLDICARBOXYLATE AND SILYBIN

FIELD OF THE INVENTION

This is a National Stage application under 35 U.S.C. § 371 of PCT/KR2004/002698 filed Oct. 21, 2004, which claims priority to Korean Patent Application 10-2003-0073462 filed on Oct. 21, 2003,l all of which are incorporated herein by reference.

The present invention relates to an oral microemulsion composition for treating liver diseases, comprising biphenyldimethyldicarboxylate (BDD) and silybin or a derivative thereof, as active ingredients.

BACKGROUND OF THE INVENTION

Biphenyldimethyldicarboxylate (BDD), a synthetic derivative of Schizandrin C which is one of the active ingredients isolated from *Schizandra chinensis*, has been known to lower the SGPT (serum glutamic pyruvic transaminase) level of a patient administered therewith, and accordingly, it is useful for treating liver diseases including acute/chronic viral hepatitis, a chronic liver disease and liver impairment by drug toxicity. (see [H. S. Lee, M. D., Y T. Kim, M. D. et al., "Prospective, randomized, controlled trial with biphenyl-dimethyl-dicarboxylate in chronic active liver diseases; The effect on lowering serum alanine aminotransferase levels, Dept. Of Internal Medicine and Liver Research Institute, Seoul Nat'l Univ. College Of Medicine, Seoul, Korea]).

Further, silybin, the primary component of a *Carduus marianus* extract, is known to have excellent activity in protecting liver cells from harmful effects caused by smoking, drinking, overworking, environmental contaminants, stress or liver-damaging drugs, and regenerating the liver cells. However, the bioavailability of orally administered BDD or silybin is unsatisfactorily low due to their low solubilities in water.

Liver diseases are caused mostly by a combination of many different factors, and therefore, a satisfactory therapeutic result cannot be obtained when a drug having a certain working mechanism is used alone. Nevertheless, the administration of a combination of two or more drugs may give rise to an undesirable side effect or antagonism induced by physical or chemical interactions between the drugs.

Accordingly, there has existed a need to develop an improved oral composition for treating liver diseases, which comprises two or more kinds of drugs having entirely different working mechanisms, has high in vivo bioavailabilities of the drugs, and causes no harmful side effects.

SUMMARY OF THE INVENTION

It is, therefore, a primary object of the present invention to provide an oral microemulsion composition comprising both biphenyldimethyldicarboxylate and silybin as active ingredients.

In accordance with one aspect of the present invention, there is provided an oral microemulsion composition for treating a liver disease, which comprises biphenyldimethyldicarboxylate (BDD) and silybin or a derivative thereof, or a *Carduus marianus* extract containing silybin and derivatives thereof, as active ingredients; a co-surfactant; a surfactant; and an oil.

DETAILED DESCRIPTION OF THE INVENTION

The inventive composition is characterized by comprising biphenyldimethyldicarboxylate and silybin or a derivative thereof, or a *Carduus marianus* extract containing silybin and derivatives thereof, as active ingredients in a stable emulsion form, thereby providing a greatly increased in vivo bioavailabilities of both of the active ingredients.

The respective components employed in the preparation of the inventive microemulsion composition are described as follows.

(1) Active Ingredient

In the present invention, water-insoluble biphenyldiimethyldicarboxylate, and a *Carduus marianus* extract, or silybin or a silybin derivative isolated therefrom, are used as active ingredients. Representative examples of the silybin derivative include silycristin, silydiamin and isosilybin. A commercially available *Carduus marianus*extract typically contains silybin in an amount of about 30% by weight or more. For instance, the *Carduus marianus* extract of IVAX Co. (Czech) contains 42% by weight of silybin, while that of Zhejiang Hengdian Co. (China), 33% by weight of sillybin.

(2) Co-Surfactant

The inventive composition contains an organic solvent as a co-surfactant, which is amphipathic, i.e., both hydrophilic and hydrophobic. The co-surfactant serves to emulsify the sparingly water-soluble active ingredients and sustain the emulsified form of the active ingredients stable during storage. Representative examples of the co-surfactant include ethanol, propyleneglycol (1,2-dihydroxypropane), polyethyleneglycol (preferably having a molecular weight of 200 to 600), propylene carbonate (4-methyl-2-oxo-1,3-dioxolane), transcutol (diethyleneglycol monoethylether), glycofurol (tetrahydrofurfuryl alcohol polyethyleneglycol ether), dimethyl isosorbide (1,4:3,6-dianhydro-2,5-dimethyl-D-glucitol) and a mixture thereof, wherein transcutol is preferred.

(3) Surfactant

The surfactant used in the present invention plays the role of emulsifying an oil in water with the aid of the co-surfactant to form a stable microemulsion and it may be any one of the pharmaceutically acceptable anionic, cationic, non-ionic or amphoteric surfactants.

Representative examples of the surfactant include:

① polyoxyethylene glycolated natural or hydrogenated vegetable oils such as polyoxyethylene glycolated natural or hydrogenated castor oil (Cremophor®, BASF; and HCO®, Nikkol), ② polyoxyethylene-sorbitan-fatty acid esters wherein fatty acid is mono- or tri-lauric, palmitic, stearic or oleic acid (Tween®, ICI), ③ polyoxyethylene fatty acid esters such as polyoxyethylene stearic acid ester (Myrj®, ICI), ④ polyoxyethylene-polyoxypropylene copolymer (Pluronic®, BASF), ⑤ polyoxyethylene-polyoxypropylene block copolymer (Poloxamer®, BASF), ⑥ sodium dioctyl sulfosuccinate or sodium lauryl sulfate, ⑦ phospholipids, ⑧ propylene glycol mono- or di-fatty acid esters such as propylene glycol dicaprylate, propylene glycol dilaurate, propylene glycol isostearate, propylene glycol laurate, propylene glycol ricinoleate and propylene glycol caprylic-capric acid diester (Miglyol® 840, Hûls), ⑨ trans-esterification products of natural vegetable oil triglycerides and polyalkylene polyols (Labrafil® M, Gattefosse), ⑩ mono-, di- or mono/di-glycerides such as caprylic/capric acid mono- and di-glycerides (Imwitor®, Hüls),
⑪ sorbitan fatty acid esters such as sorbitan monolauryl, sorbitan monopalmityl and sorbitan monostearyl esters (Span®, ICI), and
⑫ sterols or derivatives thereof such as cholesterol, pytosterol and cytosterol.

The above-mentioned surfactants can be used alone or in combination. Preferred are polyoxyethylene glycolated natural or hydrogenated vegetable oils, polyoxyethylene-sorbitan-fatty acid esters and a mixture thereof (4) Oil The oil may be any one of the pharmaceutically acceptable oils which are compatible with the co-surfactant and the surfactant used, which can be stably emulsified in water to form a stable microemulsion. Representative examples of the oil include:

① fatty acid triglycerides, preferably medium chain fatty acid triglycerides, such as fractionated coconut oil (Miglyol® 812N, Hüls),
② mono-, di- or mono/di-glycerides, preferably mono- or di-glycerides of oleic acid,
③ esters of fatty acids and monovalent alkanols, preferably esters of $C_{8-20}$ fatty acids and $C_{2-3}$ monovalent alkanols, such as isopropyl myristate, isopropyl palmitate, ethyl linoleate and ethyl oleate,
④ natural vegetable or animal oils such as corn oil, olive oil, soybean oil and fish oil,
⑤ carbohydrates such as squalene and squalane, and
⑥ free fatty acids, preferably oleic acid and linoleic acid in a fluid form.

The above-mentioned oil can be used alone or in combination with other oils, and medium chain fatty acid triglycerides, mono-, di- or mono/di-glycerides, esters of fatty acids, monovalent alkanols and a mixture thereof are preferred.

In the preparation of the inventive microemulsion composition, the biphenyldimethyldicarboxylate, the *Carduus marianus* extract (silybin or a silybin derivative), the co-surfactant, the surfactant and the oil may be used in amounts corresponding to a weight ratio in the range of 1:1~100 (0.3~33) 10~150:5~100:1~50, preferably, 1:5~60 (1.7~20): 20~100:10~80:5~20.

In addition, the inventive composition may comprise pharmaceutically acceptable additives for oral administration, e.g., viscosity controlling agents, aromatics, anti-oxidants (e.g., erythorbic acid and D-α-tocopherol) or preservatives, etc.

The inventive composition may be prepared by mixing and dissolving the components uniformly, and it forms emulsified microparticles having an average particle size of below 1 μm on contacting an aqueous medium.

The microemulsion composition of the present invention may be formulated into a soft or hard capsule, in accordance with any of the conventional procedures.

A typical daily dose of biphenyldimethyldicarboxylate and a *Carduus marianus* extract may range from about 3 to 120 mg/kg and 25 to 175 mg/kg, preferably 3 to 60 mg/kg and 25 to 175 mg/kg, respectively, and can be administered in a single dose or in divided doses. However, it should be understood that the amount of the active ingredients actually administered ought to be determined in light of various relevant factors including the condition to be treated, the age, sex and body weight of the individual patient, and the severity of the patient's symptom; and, therefore, the above dose should not be intended to limit the scope of the invention in any way.

The following Examples are intended to further illustrate the present invention without limiting its scope.

EXAMPLE 1

Preparation of a Soft Capsule Containing a Microemulsion Composition

A soft capsule was prepared using the following ingredients:

|  | Quantity (mg/capsule) |
|---|---|
| *Carduus marianus* extract (as silybin) | 120 (36) |
| BDD | 3 |
| Transcutol | 315 |
| HCO ® 50 | 170 |
| Tween ® 20 | 130 |
| Erythorbic acid | 8 |
| Miglyol ® 812N | 12 |
| Ethyl linoleate | 45 |
| Glyceril mono-oleate | 20 |
| D-a-tocopherol | 7 |

Biphenyldimethyldicarboxylate (BDD) and *Carduus marianus* extract (IVAX, Czech, silybin content: 42 wt %) were dissolved in transcutol uniformly, and other ingredients were dissolved therein, to obtain a micro-emulsion pre-concentrate. Then, the resulting pre-concentrate was used to fill a soft capsule in accordance with the conventional method described in the General Preparation Rule of the Korean Pharmacopoeia. The soft capsule was prepared using succinic acid, gelatin, glycerin and purified water by a conventional method.

EXAMPLE 2

Preparation of a Soft Capsule Containing a Microemulsion Composition

A soft capsule was prepared by the procedure of Example 1 using the following ingredients:

|  | Quantity (mg/capsule) |
|---|---|
| *Carduus marianus* extract (as silybin) | 60 (18) |
| BDD | 3 |
| Transcutol | 200 |
| HCO ® 50 | 150 |
| Tween ® 20 | 100 |
| Erythorbic acid | 8 |
| Miglyol ® 812N | 10 |
| Ethyl linoleate | 30 |
| Glyceril mono-oleate | 10 |
| D-a-tocopherol | 5 |

EXAMPLE 3

Preparation of a Soft Capsule Containing a Microemulsion Composition

A soft capsule was prepared by the procedure of Example 1 using the following ingredients:

|  | Quantity (mg/capsule) |
|---|---|
| *Carduus marianus* extract (as silybin) | 175 (52.5) |
| BDD | 3 |
| Transcutol | 460 |
| HCO ® 50 | 246 |
| Tween ® 20 | 188 |
| Erythorbic acid | 10 |
| Miglyol ® 812N | 17 |
| Ethyl linoleate | 65 |
| Glyceril mono-oleate | 29 |
| D-a-tocopherol | 10 |

EXAMPLE 4

Preparation of a Soft Capsule Containing a Microemulsion Composition

A soft capsule was prepared by the procedure of Example 1 using the following ingredients:

|  | Quantity (mg/capsule) |
|---|---|
| *Carduus marianus* extract (as silybin) | 175 (52.5) |
| BDD | 25 |
| Transcutol | 600 |
| HCO ® 50 | 220 |
| Tween ® 20 | 1170 |
| Miglyol ® 812N | 20 |
| Ethyl linoleate | 20 |
| Glyceril mono-oleate | 50 |
| D-a-tocopherol | 10 |

EXAMPLE 5

Preparation of a Soft Capsule Containing a Microemulsion Composition

A soft capsule was prepared by the procedure of Example 1 using the following ingredients:

|  | Quantity (mg/capsule) |
|---|---|
| *Carduus marianus* extract (as silybin) | 120 (36) |
| BDD | 3 |
| Dimethyl isosorbide | 310 |
| HCO ® 50 | 160 |
| Poloxamer ® | 130 |
| Miglyol ® 812N | 40 |
| Oleic acid | 20 |
| Glyceril mono-oleate | 40 |
| D-a-tocopherol | 6 |

EXAMPLE 6

Preparation of a Soft Capsule Containing a Microemulsion Composition

A soft capsule was prepared by the procedure of Example 1 using the following ingredients:

|  | Quantity (mg/capsule) |
|---|---|
| *Carduus marianus* extract (as silybin) | 120 (36) |
| BDD | 7.5 |
| Transcutol | 340 |
| HCO ® 50 | 180 |
| Tween ® 20 | 150 |
| Erythorbic acid | 9 |
| Miglyol ® 812N | 18 |
| Ethyl linoleate | 60 |
| Glyceril mono-oleate | 20 |
| D-a-tocopherol | 10 |

TEST EXAMPLE 1

Therapeutic Effect on the Liver Damaged by Carbon Tetrachloride

The therapeutic effect of the inventive oral microemulsion composition on the liver damaged by $CCl_4$ was examined as follows.

Thirty-six 4 to 5-week old male Sprague Dawley rats were divided into six groups each consisting of 6 rats having an average body weight of 202±5g. The rats were acclimated to the cage environment set at 23±2° C. and 55±5% relative humidity. Then 50% (v/v) solution of carbon tetrachloride in corn oil was intraperitoneally administered to each rat of five experimental groups (Groups 1 to 5) at a dose of 0.75 ml/kg, twice a week (monday and friday) to induce hepatotoxicity.

The rats of Group 1 (negative control) were not treated with any therapeutic drug after the $CCl_4$ injection. The rats of Group 2 (positive control) were orally administered with BDD suspended in 1% (w/v) CMC (carboxymethyl cellulose) once a day, six times a week after the $CCl_4$ injection, in an amount corresponding to 25 mg/kg of BDD; the rats of Group 3, with a *Carduus marianus* extract suspended in 1% (w/v) CMC, in an amount corresponding to 175 mg/kg of the *Carduus marianus* extract (52.5 mg/kg as silybin); and the rats of Group 4, with a simple mixture of BDD and *Carduus marianus* extract suspended in 1% (w/v) CMC, in an amount corresponding to 25 mg/kg of BDD and 175 mg/kg of the *Carduus marianus* extract. The rats of Group 5 were orally administered with the formulation of Example 3 once a day, six times a week, in an amount corresponding to 3 mg/kg of BDD and 175 mg/kg of the *Carduus marianus* extract; and the rats of Group 6 (normal group) were not subjected to $CCl_4$ injection and no therapeutic drugs were administered thereto.

Four weeks after the administration, the rats were sacrificed and serum samples were taken according to a preset schedule. The serum ALT (alanine aminotransferase) and AST (aspartate aminotransferase) levels were measured in accordance with a conventional method, and the results are shown in Tables 1 and 2, respectively.

TABLE 1

| Animal group | ALT* (SF U/ml) | Ratio of ALT level to a control (%) |
|---|---|---|
| Group 1 (control) | 150.2 ± 26.0 | 100 |
| Group 2 (BDD) | 137.7 ± 19.5 | 91.7 |
| Group 3 (silybin) | 129.8 ± 10.1 | 86.4 |
| Group 4 (BDD + silybin) | 90.1 ± 7.3 | 59.9 |
| Group 5 (Example 3) | 50.3 ± 8.4 | 33.5 |

TABLE 1-continued

| Animal group | ALT* (SF U/ml) | Ratio of ALT level to a control (%) |
|---|---|---|
| Group 6 (normal) | 30.5 ± 5.8 | — |

*an average concentration of ALT ± standard deviation

TABLE 2

| Animal group | AST* (SF U/ml) | Ratio of AST level to a control (%) |
|---|---|---|
| Group 1 (control) | 171.5 ± 11.9 | 100 |
| Group 2 (BDD) | 163.3 ± 4.5 | 95.2 |
| Group 3 (silybin) | 158.6 ± 8.6 | 92.4 |
| Group 4 (BDD + silybin) | 112.1 ± 6.1 | 65.4 |
| Group 5 (Example 3) | 80.1 ± 8.5 | 46.7 |
| Group 6 (normal) | 66.2 ± 15.3 | — |

*an average concentration of AST ± standard deviation

As shown in Tables 1 and 2, for Group 4 (BDD+silybin) and Group 5 (Example 3) administered with BDD and silybin simultaneously, the increase in the ALT and AST levels induced by $CCl_4$ was lower by a factor 2 to 3 as compared with Group 2 (BDD) or Group 3 (silybin).

The inventive microemulsion preparation (Group 5) containing the two active ingredients in an emulsified form, in particular, exhibited a much higher inhibitory effect than that observed for the simple mixture of BDD and silybin (Group 4), in spite of the fact that the amount of BDD administered to Group 5 was less than Group 4.

These results demonstrate that the inventive microemulsion preparation has a superior therapeutic effect on $CCl_4$-induced liver damage owing to the enhanced bioavailabilities of both of the active ingredients contained therein.

TEST EXAMPLE 2

Dose-dependent Therapeutic Effect on the $CCl_4$-induced Liver Damage

In order to examine the change in the therapeutic effect of the inventive oral microemulsion composition with the doses of the active ingredients, tests on the $CCl_4$-damaged liver were conducted as follows.

Hepatotoxicity was induced in rats by carbon tetrachloride administration according to the procedure of Test Example 1, except that five groups of Sprague Dawley rats each consisting of 6 rats were used.

The rats of Group 1 (negative control) were not treated with any therapeutic drug after the $CCl_4$ injection; and the rats of Groups 2 to 4 were orally administered with the formulation prepared in Examples 2, 1 and 3, respectively, once a day, six times a week at a dosage of one capsule/kg, after the $CCl_4$ injection. The rats of Group 5 (normal group) received neither $CCl_4$ injection nor a therapeutic drug.

Four weeks after the administration, the serum ALT and AST levels were measured, and the results are shown in Tables 3 and 4, respectively.

TABLE 3

| Animal group | ALT* (SF U/ml) | Ratio of ALT level to a control (%) |
|---|---|---|
| Group 1 (control) | 130.8 ± 10.0 | 100 |

TABLE 3-continued

| Animal group | ALT* (SF U/ml) | Ratio of ALT level to a control (%) |
|---|---|---|
| Group 2 (Example 2) | 82.5 ± 8.6 | 63.1 |
| Group 3 (Example 1) | 63.2 ± 6.5 | 48.3 |
| Group 4 (Example 3) | 65.4 ± 7.5 | 50.0 |
| Group 5 (normal) | 30.6 ± 4.3 | — |

*an average concentration of ALT ± standard deviation

TABLE 4

| Animal group | AST* (SF U/ml) | Ratio of AST level to a control (%) |
|---|---|---|
| Group 1 (control) | 213.7 ± 19.5 | 100 |
| Group 2 (Example 2) | 133.3 ± 8.7 | 62.4 |
| Group 3 (Example 1) | 119.9 ± 10.3 | 56.1 |
| Group 4 (Example 3) | 109.8 ± 5.9 | 51.4 |
| Group 5 (normal) | 78.7 ± 3.3 | — |

*an average concentration of AST ± standard deviation

As shown in Tables 3 and 4, the inhibitory effect of the inventive microemulsion preparation against the increase in the serum ALT and AST levels depends on the dosages of the active ingredients, BDD and *Carduus marianus* extract. If the *Carduus marianus* extract/BDD ratio (w/w) is more than 40, the effect remains more or less unchanged.

TEST EXAMPLE 3

Therapeutic Effect on the dl-ethionine-induced Fatty Liver

In order to examine the therapeutic effect of the inventive oral microemulsion composition, a test to measure the activity of restoring fatty liver induced by dl-ethionine was conducted as follows.

Six groups of rats, each consisting of 6 rats were prepared by the procedure of Test Example 1. A 2% (w/v) dl-ethionine saline solution was subcutaneously injected to each rat of five experimental groups (Groups 1 to 5) at a dosage of 200 mg/kg, twice a week to induce fatty liver.

The rats of Group 1 (negative control) were not treated with any therapeutic drug after the ethionine injection. The rats of Group 2 (positive control) were orally administered with BDD suspended in 1% (w/v) CMC once a day, five times a week after the ethionine injection, in an amount corresponding to 25 mg/kg of BDD; the rats of Group 3, with the *Carduus marianus* extract suspended in 1% (w/v) CMC, in an amount corresponding to 175 mg/kg of the *Carduus marianus* extract (52.5 mg/kg as silybin); and the rats of Group 4, with a simple mixture of BDD and *Carduus marianus* extract suspended in 1% (w/v) CMC, in an amount corresponding to 25mg/kg of BDD and 175 mg/kg of the *Carduus marianus* extract. The rats of Group 5 were orally administered with the formulation of Example 3 once a day, five times a week, in an amount corresponding to 3 mg/kg of BDD and 175 mg/kg of the *Carduus marianus* extract; and the rats of Group 6 (normal group) received neither ethionine injection nor any therapeutic drug.

One week after the administration, each rat was sacrificed, and the liver was extracted therefrom. The extracted liver was washed with saline, soaked in a 4-fold volume of potassium phosphate buffer (pH 7.5), and homogenized with a teflone-glass homogenizer. The homogenized liver was subjected to centrifugation at 600×g for 10 minutes to obtain a supernatant, which was subjected to centrifugations at 10,000×g for 20minutes, and then at 10,000×g for 1 hour, to obtain a supernatant.

Then, the total cholesterol and triglyceride levels of each liver sample were measured by employing the supernatant in accordance with a conventional method, and the results are shown in Tables 5 and 6, respectively.

TABLE 5

| Animal group | Total Cholesterol* (mg/g) | Ratio of cholesterol level to a control (%) |
| --- | --- | --- |
| Group 1 (control) | 24.1 ± 1.4 | 100 |
| Group 2 (BDD) | 22.0 ± 1.9 | 91.3 |
| Group 3 (silybin) | 21.3 ± 3.5 | 88.4 |
| Group 4 (BDD + silybin) | 20.3 ± 2.9 | 84.2 |
| Group 5 (Example 3) | 18.7 ± 3.7 | 77.6 |
| Group 6 (normal) | 17.2 ± 2.7 | — |

*an average concentration of total cholesterol ± standard deviation

TABLE 6

| Animal group | Triglyceride* (mg/g) | Ratio of triglylceride level to a control (%) |
| --- | --- | --- |
| Group 1 (control) | 13.9 ± 2.5 | 100 |
| Group 2 (BDD) | 10.1 ± 0.5 | 72.7 |
| Group 3 (silybin) | 9.7 ± 2.5 | 69.8 |
| Group 4 (BDD + silybin) | 9.0 ± 2.2 | 64.7 |
| Group 5 (Example 3) | 7.5 ± 0.1 | 54.0 |
| Group 6 (normal) | 5.5 ± 0.5 | — |

*an average concentration of triglyceride ± standard deviation

As shown in Tables 5 and 6, for Group 4 (BDD+silybin) and Group 5(Example 3) administered with BDD and silybin in combination, the inhibitory effect against the increase in the cholesterol and triglyceride levels in the fatty liver was much higher than that of Group 2 (BDD) or Group 3(silybin).

The inventive microemulsion preparation (Group 5) containing the two active ingredients, in particular, exhibited much higher inhibitory effect than the simple mixture of BDD and silybin (Group 4), in spite of the fact that the amount of BDD administered to Group 5 was less than Group 4.

These results demonstrate that the inventive microemulsion preparation has a superior therapeutic effect on dl-ethionine-induced fatty liver owing to the enhanced bioavailabilities of both of the active ingredients contained therein.

TEST EXAMPLE 4

Dose-dependent Therapeutic Effect on the dl-ethionine-Induced Fatty Liver

In order to examine the change in the therapeutic effect of the inventive oral microemulsion composition with the doses of the active ingredients, tests on the dl-ethionine-induced fatty liver were conducted as follows.

Hepatotoxicity was induced in rats by dl-ethionine administration according to the procedure of Test Example 3, except that five groups of Sprague Dawley rats each consisting of 6 rats were used.

The rats of Group 1 (negative control) were not treated with any therapeutic drug after the ethionine injection; and the rats of Groups 2 to 4 were orally administered with the formulation prepared in Examples 2, 1 and 3, respectively, once a day, five times a week at a dosage of one capsule/kg, after the ethionine injection. The rats of Group 5 (normal group) received neither ethionine injection nor a therapeutic drug.

One week after the administration, the serum cholesterol and triglyceride levels in the liver were measured, and the results are shown in Tables 7 and 8, respectively.

TABLE 7

| Animal group | Total cholesterol* (mg/g) | Ratio of cholesterol level to a control (%) |
| --- | --- | --- |
| Group 1 (control) | 26.4 ± 2.5 | 100 |
| Group 2 (Example 2) | 21.2 ± 1.8 | 80.3 |
| Group 3 (Example 1) | 20.2 ± 1.7 | 76.5 |
| Group 4 (Example 3) | 19.8 ± 2.4 | 75 |
| Group 5 (normal) | 17.7 ± 2.2 | — |

*an average concentration of total cholesterol ± standard deviation

TABLE 8

| Animal group | Triglyceride* (mg/g) | Ratio of triglyceide level to control (%) |
| --- | --- | --- |
| Group 1 (control) | 14.0 ± 0.7 | 100 |
| Group 2 (Example 2) | 10.6 ± 0.5 | 75.7 |
| Group 3 (Example 1) | 10.0 ± 2.2 | 71.4 |
| Group 4 (Example 3) | 8.9 ± 0.4 | 63.6 |
| Group 5 (normal) | 5.5 ± 0.5 | — |

*an average concentration of triglyceride ± standard deviation

As shown in Tables 7 and 8, the inhibitory effect of the inventive microemulsion preparation against the increase in the serum cholesterol and triglyceride levels depends on the dosage of the active ingredients, BDD and *Carduus marianus* extract. If the *Carduus marianus* extract/BDD ratio (w/w) is more than 40, the effect remains more or less unchanged.

TEST EXAMPLE 5

Acute Toxicity Test

The acute toxicity of an orally administered preparation containing both BDD and silybin was examined as follows, using ICR rats having an average body weight of 20 to 25 g each.

Sample preparations were obtained by mixing BDD and silybin in various weight ratios as shown in Table 9 and each was orally administered to a group consisting of ten rats at a dose of 0.1, 0.2, 0.5, 1 and 2 g/kg. One week after the administration, the number of deceased animals was counted to calculate the death rate (%), and the results are shown in Table 9.

TABLE 9

| BDD: Silybin (weight ratio) | 0.1 g Death rate (%) | 0.2 g Death rate (%) | 0.5 g Death rate (%) | 1 g Death rate (%) | 2 g Death rate (%) |
| --- | --- | --- | --- | --- | --- |
| 1:1 | 0 | 0 | 0 | 0 | 0 |
| 1:10 | 0 | 0 | 0 | 0 | 0 |
| 1:20 | 0 | 0 | 0 | 0 | 0 |
| 1:40 | 0 | 0 | 0 | 0 | 0 |
| 1:58 | 0 | 0 | 0 | 0 | 0 |

As shown in Table 9, there was no sign of lethality or toxic responses at 2 g/kg of the preparation containing both BDD and silybin. Accordingly, it was confirmed that the composition of the present invention is not toxic and safe.

TEST EXAMPLE 6

Absorption Test

In order to examine the bioavailabilities of the active ingredients of the inventive preparation, an in vivo absorption test was carried out as follows by employing the preparation of Example 4 (Experimental preparation) and a preparation obtained by simply mixing 25 mg of BDD and 175 mg of a *Carduus marianus* extract (Comparative preparation).

Ten 14 to 15-week old male Sprague-Dawley rats (weight: about 250g each) were acclimated for more than 4 days, while allowing free access to the feed and water. The rats were then put on a 48-hour fast, while they were allowed to free access to water.

The rats were divided into two groups each consisting of five rats, and were orally administered with the experimental and comparative preparations, respectively, in an amount corresponding to 25 mg/kg of BDD and 175 mg/kg of the *Carduus marianus* extract (58 mg/kg as silybin). Blood samples were taken from the rats before administration, and 0.5, 1, 1.5, 4, 8 and 24 hours after the administration. Plasma samples were obtained from the blood samples.

The analysis for plasma BDD concentration was conducted as follows.

200 μl of methanol was added to 100 μl of plasma, and the mixture was shaken. The mixture was centrifuged at 3,000 rpm for 10 minutes to obtain a supernatant, which was then filtered through a 0.22 μm filter, and analyzed by LC-MS, under the following conditions.

Column: Waters MS C18 (2.1×150 mm with guard column)
Mobile phase: 50% methanol
Injection volume: 10 μl
Flow rate: 0.2 ml/min.
Detector: SIR mode m/z: 441.2 (Na adduct)
The results are shown in Table 10.

TABLE 10

| Preparation | AUC*1 (ng · hr/ml) | $C_{max}$*2 (ng/ml) | $T_{max}$*3 (hour) |
|---|---|---|---|
| Example 4 | 4935.7 ± 513.8 | 1198.5 ± 411.5 | 0.5 ± 0.0 |
| Comparative Preparation | 311.8 ± 115.5 | 29.7 ± 8.3 | 2.6 ± 1.7 |

*1Area under the plasma BDD concentration versus time curve integrated for 0 to 24 hours
*2Maximum plasma BDD concentration
*3Time at the maximum plasma BDD concentration The analysis for plasma silybin concentration, on the other hand, was conducted as follows.

500 μl of each serum sample was combined with 50 μl of an internal standard solution (methanol solution containing 2.0 μg/ml of naringenin), 900μl of 0.5 M sodium acetate solution (pH 5.0) and 100 μl of an enzyme solution (0.5 M sodium acetate solution (pH 5.0) of β-glucuronidase 13.48units/sulphatase 4.5 units), mixed for 5 minutes, and the mixture was kept at 37° C. for 4 hours. 1.5 ml of 1 M sodium carbonate (pH 8.5) was added thereto, shaken for 10 minutes, 5 ml of ether was added thereto, and the resulting mixture was shaken for 15 minutes to obtain an extract. The extract was centrifuged at 2,000 rpm for 10 minutes to obtain a supernatant, and 4.2ml of the supernatant was condensed 30° C. under a nitrogen atmosphere. The resulting residue was combined with 250 μl of a mixture of methanol and 10 mM sodium dihydrogen phosphate (50:50) and the mixture was subjected to HPLC under the following conditions.

Column: Inertsil ODS2 (5 μm, 4.6×250 mm)
Mobile phase: methanol: 10 mM sodium dihydrogen phosphate=50:50 (v:v, pH 3.0 by phosphoric acid)
injection volume: 50 μl
flow rate: 1.0 ml/min.
Detector: UV 285 nm
The results are shown in Table 11.

TABLE 11

| Preparation | AUC*1 (ng · hr/ml) | $C_{max}$*2 (ng/ml) | $T_{max}$*3 (hour) |
|---|---|---|---|
| Example 4 | 115.3 ± 9.8 | 43.1 ± 6.7 | 0.8 ± 0.3 |
| Comparative Preparation | 8.9 ± 3.3 | 2.3 ± 1.1 | 1.1 ± 0.2 |

*1Area under the plasma silybin concentration versus time curve integrated for 0 to 24 hours
*2Maximum plasma silybin concentration
*3Time at the maximum plasma silybin concentration As shown in Tables 10 and 11, the bioavailabilities of BDD and silybin observed in the inventive preparation are much higher than those of the comparative preparation, by about factors of 15 and 10, respectively.

While the invention has been described with respect to the above specific embodiments, it should be recognized that various modifications and changes may be made to the invention by those skilled in the art which also fall within the scope of the invention as defined by the appended claims.

What is claimed is:

1. An oral microemulsion composition for treating a liver disease, which comprises biphenyldimethyldicarboxylate (BDD) and silybin or a derivative thereof, or a *Carduus marianus* extract containing silybin and a derivative thereof, as active ingredients; a co-surfactant; a surfactant; and an oil, wherein the silybin derivative is silycristin, silydiamin or isosilybin; and wherein the biphenyldimethyldicarboxylate: the silybin or silybin derivative: co-surfactant: surfactant: oil ratio by weight is in the range of 1:0.3~33:10~150:5~100: 1~50, or wherein the biphenyldimethyldicarboxylate: *Carduus marianus* extract: co-surfactant: surfactant: oil ratio by weight is in the range of 1:1~100:10~150:5~100:1~50.

2. The oral microemulsion composition of claim 1, wherein the co-surfactant is selected from the group consisting of ethanol, propyleneglycol, polyethyleneglycol, propylene carbonate, transcutol, glycofurol, dimethyl isosorbide and a mixture thereof.

3. The oral microemulsion composition of claim 2, wherein the co-surfactant is transcutol.

4. The oral microemulsion composition of claim 1, wherein the surfactant is selected from the group consisting of: polyoxyethylene glycolated natural or hydrogenated vegetable oils, polyoxyethylene-sorbitan-fatty acid esters, polyoxyethylene fatty acid esters; polyoxyethylene-polyoxypropylene copolymers; polyoxyethylene-polyoxypropylene block copolymers; sodium dioctyl sulfosuccinate; sodium lauryl sulfate; phospholipids; propylene glycol mono- or di-fatty acid esters; trans-esterification products of natural vegetable oil triglycerides and polyalkylene polyols; mono-, di- or mono/di-glycerides, sorbitan fatty acid esters; sterols or derivatives thereof; and a mixture thereof.

5. The oral microemulsion composition of claim 4, wherein the surfactant is selected from the group consisting of polyoxyethylene glycolated natural or hydrogenated vegetable oils, polyoxyethylene-sorbitan-fatty acid esters and a mixture thereof.

6. The oral microemulsion composition of claim 1, wherein the oil is selected from the group consisting of: medium chain fatty acid triglycerides; mono-, di- or mono/di-glycerides; monovalent alkanol esters of fatty acids; natural vegetable or animal oils; squalene; squalane; oleic acid; linoleic acid; and a mixture thereof.

7. The oral microemulsion composition of claim 6, wherein the oil is selected from the group consisting of medium chain fatty acid triglycerides, mono-, di- or mono/di-glycerides, esters of fatty acids and monovalent alkanols and a mixture thereof.

8. The oral microemulsion composition of claim 1, which forms microparticles having an average particle size of less than 1 μm upon contact with an aqueous medium.

* * * * *